(12) United States Patent
James, Jr.

(10) Patent No.: US 8,146,601 B2
(45) Date of Patent: Apr. 3, 2012

(54) MEDICAL BITE BLOCK AND ASSOCIATED METHODS

(76) Inventor: John M. James, Jr., Maitland, FL (US)

(*) Notice: Subject to any disclaimer, the term of this patent is extended or adjusted under 35 U.S.C. 154(b) by 291 days.

(21) Appl. No.: 12/500,324

(22) Filed: Jul. 9, 2009

(65) Prior Publication Data

US 2010/0006110 A1    Jan. 14, 2010

Related U.S. Application Data

(60) Provisional application No. 61/079,267, filed on Jul. 9, 2008.

(51) Int. Cl.
 *B63C 11/02* (2006.01)
 *A61M 16/00* (2006.01)
 *A62B 18/02* (2006.01)
 *A62B 18/08* (2006.01)

(52) U.S. Cl. ........ 128/861; 128/846; 128/848; 128/857; 128/859; 128/201.27; 128/203.29; 128/205.25; 128/206.12; 128/206.21; 433/6; 433/7; 602/902

(58) Field of Classification Search ............... 433/6, 7, 433/37–48; 128/846, 848, 857, 859–862, 128/201.27, 203.29, 205.25, 206.12, 206.21; 602/902
See application file for complete search history.

(56) References Cited

U.S. PATENT DOCUMENTS

| | | | |
|---|---|---|---|
| 1,500,107 A | 7/1924 | Chandler | |
| 4,179,815 A * | 12/1979 | Hoffman | 433/140 |
| 4,425,911 A | 1/1984 | Luomanen et al. | 128/200.26 |
| 4,445,854 A * | 5/1984 | Bekey et al. | 433/37 |
| 4,495,945 A | 1/1985 | Liegner | 128/200.26 |
| 4,975,057 A | 12/1990 | Dyfvermark | 433/93 |
| 5,069,619 A * | 12/1991 | Frisbie | 433/72 |
| 5,386,821 A | 2/1995 | Poterack | 128/200.26 |
| 5,462,066 A * | 10/1995 | Snyder | 128/848 |
| 5,655,519 A | 8/1997 | Alfery | 128/200.26 |
| 6,152,733 A | 11/2000 | Hegemann et al. | 433/80 |
| 6,244,866 B1 | 6/2001 | Campbell | 433/140 |
| 6,652,276 B2 | 11/2003 | Fischer et al. | 433/140 |
| 6,716,029 B2 | 4/2004 | Fischer et al. | 433/140 |

(Continued)

OTHER PUBLICATIONS

Flex Blue Bite Block, King Systems, Airway Control. Airway Solutions. www.kingsystems.com/PRODUCTS/AirwayDevices/FlexBlueBiteBlock/tabid/164/Default.aspx, downloaded Nov. 4, 2009.

*Primary Examiner* — Patricia Bianco
*Assistant Examiner* — Brandon Jackson
(74) *Attorney, Agent, or Firm* — Allen, Dyer, Doppelt, Milbrath & Gilchrist, P.A.

(57) ABSTRACT

A bite block is to be positioned between opposing upper and lower teeth in a patient's mouth. The bite block includes an elongate member having a top and a bottom. First and second sidewalls are coupled to the elongate member on opposite sides thereof. Each sidewall extends above and below the top and bottom of the elongate member to define upper and lower teeth spaced apart transverse notches defined in an upper surface thereof. In addition, the second sidewall has a second set of spaced apart receiving channels. The first sidewall has a first set of transverse notches defined in an upper surface thereof. The first sidewall may also have a third set of spaced apart transverse notches defined in a lower surface thereof. In addition, the second sidewall may also have a fourth set of spaced apart transverse notches defined in a lower surface thereof.

20 Claims, 6 Drawing Sheets

U.S. PATENT DOCUMENTS

| | | | |
|---|---|---|---|
| 6,964,568 B1 * | 11/2005 | Segal | 433/45 |
| 6,966,319 B2 | 11/2005 | Fitton | 128/848 |
| 7,293,990 B2 | 11/2007 | Hirsch et al. | 433/93 |
| 7,690,918 B2 * | 4/2010 | Ho et al. | 433/45 |
| 2006/0110705 A1 | 5/2006 | Jensen et al. | 433/140 |
| 2007/0218421 A1 * | 9/2007 | Narang et al. | 433/136 |
| 2008/0090200 A1 | 4/2008 | Hirsch et al. | 433/29 |
| 2008/0178892 A1 | 7/2008 | Haduong | 128/845 |
| 2008/0230055 A1 | 9/2008 | Napier | 128/200.26 |

* cited by examiner

MEDICAL BITE BLOCK AND ASSOCIATED METHODS

RELATED APPLICATION

This application is based upon prior filed provisional application Ser. No. 61/079,267 filed Jul. 9, 2008, the entire subject matter of which is incorporated herein by reference in its entirety.

FIELD OF THE INVENTION

The present invention relates to the field of anesthesiology, and, more particularly, to devices that help prevent damage caused by an involuntary clenching of an anesthetized patient's teeth and related methods.

BACKGROUND OF THE INVENTION

A medical practitioner will typically secure the airway of a patient undergoing general anesthesia to ensure proper airway ventilation. Common methods of providing proper airway ventilation include the use of an endotracheal tube (ETT) or a laryngeal mask airway (LMA). An ETT is a plastic tube that is inserted through the mouth into a patient's trachea to ensure that the airway is not closed off and that air is able to reach the lungs. An LMA is a plastic tube having an inflatable cuff at one end to be inserted through the mouth into the hypopharynx where it sits tightly over the top of the larynx.

Several problems are posed by the use of either an ETT or an LMA in an anesthetized patient. First, a patient may unconsciously and involuntarily bite down on the tube and occlude the airflow, usually during emergence (waking up) from anesthesia. This may lead to hypoxemia, a low blood oxygen level. Such occlusion of the airflow may delay the emergence from anesthetic inhalation agents and can even lead to negative pressure pulmonary edema (NPEE). NPEE may occur when the patient struggles to inhale against a partially or completely occluded upper airway. In a vigorous adult the inspiratory muscles can generate enough negative pressure to cause fluid to extravasate from the pulmonary capillaries into the interstitial and alveolar spaces. This fluid leak may result in immediate or delayed hypoxemia. Even after an upper airway obstruction is alleviated, pulmonary edema can develop immediately or up to six hours later. Second, a patient may bite down with enough force to damage the anterior teeth in contact with the ETT or LMA, especially when veneers or bridges are in employ as dental restorations or in a patient with loose or unstable anterior teeth.

Medical practitioners typically place a "homemade" roll of gauze, or sometimes a roll of gauze wrapped in tape, between a patient's molar teeth to help prevent occlusion of the ETT or LMA when the patient involuntarily bites down. However, this may be an unsatisfactory approach because the gauze can slip out of place or alternatively be compressed down with involuntary biting thereby allowing the ETT or LMA airway to be compressed and occlusion thereof to occur.

A dental bite block may also be unsatisfactory because it is designed for use on awake patients and is designed to keep the mouth opened wide for access to posterior teeth. Furthermore, a dental bite block is typically small and completely intra-oral in application and could fall into the back of the throat during ETT or LMA removal, resulting in gagging or airway obstruction, and may also prove difficult to extract from the patient's mouth after removal of the ETT or LMA.

Bite blocks designed for endoscopy are designed to reside anteriorly between the incisors of the patient, and are unsuitable for anesthetized patients as biting forces will be applied to the incisors. The incisors are. less suited than molar teeth to withstanding the forces generated in clenching of the jaws in anesthetized patients, increasing the risk of dental injury.

A prior attempt at producing a bite block compatible with an ETT or an LMA is disclosed in U.S. Pat. No. 5,655,519 to Alfery. Alfery discloses a wedge shaped bite block having upper and lower non-incisor teeth engagement surfaces. The bite block is angled such that the non-incisor teeth engagement surfaces gradually become farther apart in a direction from the posterior portion toward the anterior portion, to thereby hold a patient's incisors apart when the bite block is positioned in the patient's mouth at one side thereof. Two pairs of spaced apart flanges extend from the bite block to limit lateral movement of the bite block in the patient's mouth. A handle is included for facilitating positioning of the bite block within the patient's mouth and for removing the bite block. Alfrey's design has a drawback in that it is complex to manufacture as it uses different materials for construction of the handle and the teeth interfacing aspect, respectively. This may render the bite block too expensive for disposable use. In addition, it is unclear as to how the handle is anchored to the teeth interfacing portion, creating concern that the two may become separated during clinical use leaving the smaller teeth-interfacing portion loose in the mouth. This would create a risk of dislodgement and loss of the bite block into the patient's pharynx and the potential for subsequent airway obstruction, and then the small nature of this portion of the bite block could be difficult to retrieve and remove. In addition, the handle may prove cumbersome and impractical in routine use in anesthetized patients, especially in patients undergoing head or neck surgery, or in those patients who require prone positioning, for example in spinal surgery. Lastly, the flanges in Alfery's device are elongated and may rest against the gingiva of the patient and, in surgeries requiring an hour or more, this could contribute to gingival compression injuries.

Another bite block is shown at www.kingsystems.com/PRODUCTS/AirwayDevices/FlexBlueBiteBlock/tabid/164/Default.aspx. This bite block may, however be unstable when placed in a patient's mouth due to its semicircular molar engaging surfaces.

A further attempt at a bite block is described in U.S. Pat. No. 4,495,945 to Liegner, which discloses a bite block for use in an endoscopy procedure. This bite block has teeth receiving channels that are in contact with all of the patient's teeth. As such, when a patient bites down, the bite force is distributed among all the patient's teeth, including weaker teeth such as the lateral incisors and canines. This may lead to damage of these teeth.

U.S. Pat. No. 5,386,821 to Poterack described a bilateral bite block for use in a patient's mouth with an ETT in place. A handle connects the two sides of the bite block, but the molar interfacing surfaces are angled in a manner that may allow displacement of the sides laterally into the cheek pouches. This might result in contact between the patient's molar and a loss of function of the bite block.

SUMMARY OF THE INVENTION

In view of the foregoing background, it is therefore an object of the present invention to provide a simple to manufacture bite block that will remain securely in place in a patient's mouth and help reduce the chances of molar apposition.

This and other objects, features, and advantages in accordance with the present invention are provided by a bite block to be positioned between opposing upper and lower teeth in a patient's mouth. The bite block may be positioned between opposing upper and lower molar teeth, for example. The bite block may comprise an elongate member having a top and a bottom. First and second sidewalls may be coupled to the elongate member on opposite sides thereof, and each sidewall may extend above and below the top and bottom of the elongate member to define upper and lower teeth receiving channels.

The first sidewall may have a first set of spaced apart transverse notches defined in an upper surface thereof, and the second sidewall may have a second set of spaced apart transverse notches defined in an upper surface thereof. These spaced apart transverse notches may receive the patient's teeth and thereby help keep the bite block securely located in the patient's mouth. The bite block will remain securely in place and reduce the chance of damage to a patient's teeth, is nearly foolproof in its application, and is of sufficiently simple design to be easily and cost effectively manufactured as a single use disposable device.

The first sidewall may have a third set of spaced apart transverse notches defined in a lower surface thereof. In addition, the second sidewall may also have a fourth set of spaced apart transverse notches defined in a lower surface thereof.

The first set of spaced apart transverse notches may be canted at an angle from perpendicular to the elongate member and the second set of spaced apart transverse notches may be canted at an opposite angle to the first set of transverse notches. The canted nature of the notches may allow the patient's canine and/or lateral incisor teeth to rest within the notch, thereby facilitating a reasonable anchoring or fixation of the bite block in the patient's mouth in a desired and intended anatomical position, and in so doing may decrease the likelihood that the bite block will slip out of the mouth when at rest or when the patient bites down.

The first and second sidewalls may have rounded top and bottom surfaces. The elongate member, the first sidewall, and the second sidewall may be integrally molded as a monolithic unit. The elongate member, the first sidewall, and the second sidewall may comprise a compliant material. In some applications, the compliant material may be foam rubber or silicone rubber. In addition, an absorbent layer may surround the elongate member, the first sidewall, and the second sidewall.

The elongate member may have a first end, a second end, and a medial portion therebetween. The first end may protrude from the patient's mouth when the bite block is inserted therein. The elongate member may taper downwardly in thickness from the first end to the second end. In another embodiment, the second end may have a thickness greater than the first end, and the medial portion may have a thickness greater than the second end and the first end. In addition, there may be indicia on the elongate member indicating a desired orientation for the bite block in the patient's mouth.

The first and second sidewalls may be of a limited height to minimize contact with the patient's gingiva. This may reduce the risk of gingival compression irritation when the bite block is placed in the intended anatomic position in the patient's mouth for an extended period of time.

A method aspect is directed to a method of making a bite block to be positioned between opposing upper and lower teeth, for example molar teeth, in a patient's mouth. The method may include forming an elongate member having a top and a bottom. First and second sidewalls may be formed coupled to the elongate member on opposite sides thereof, each sidewall extending above and below the top and bottom of the elongate member to define upper and lower teeth receiving channels. A first set of spaced apart transverse notches may be defined in an upper surface of the first sidewall. Further, a second set of spaced apart transverse notches may be defined in an upper surface of the second sidewall.

BRIEF DESCRIPTION OF THE DRAWINGS

FIG. 5b is a top view of the medical bite block of FIG. 5a.
FIG. 5c is a side view of the medical bite block of FIG. 5a.
FIG. 5d is a front view of the medical bite block of FIG. 5a.
FIG. 5e is a rear view of the medical bite block of FIG. 5a.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
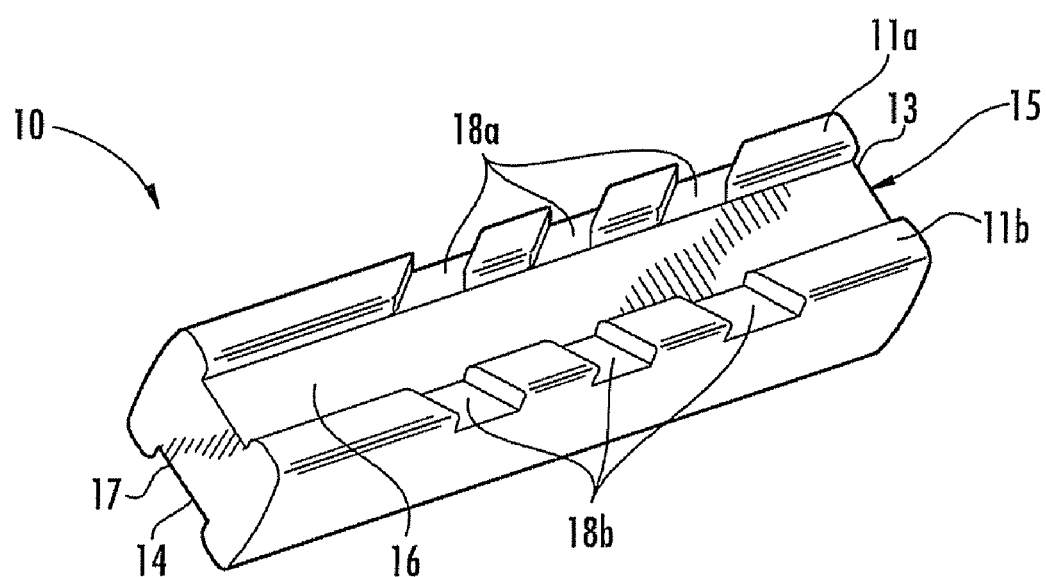
FIG. 1 is a perspective side view of a medical bite block in accordance with the present invention.
Figure 2:
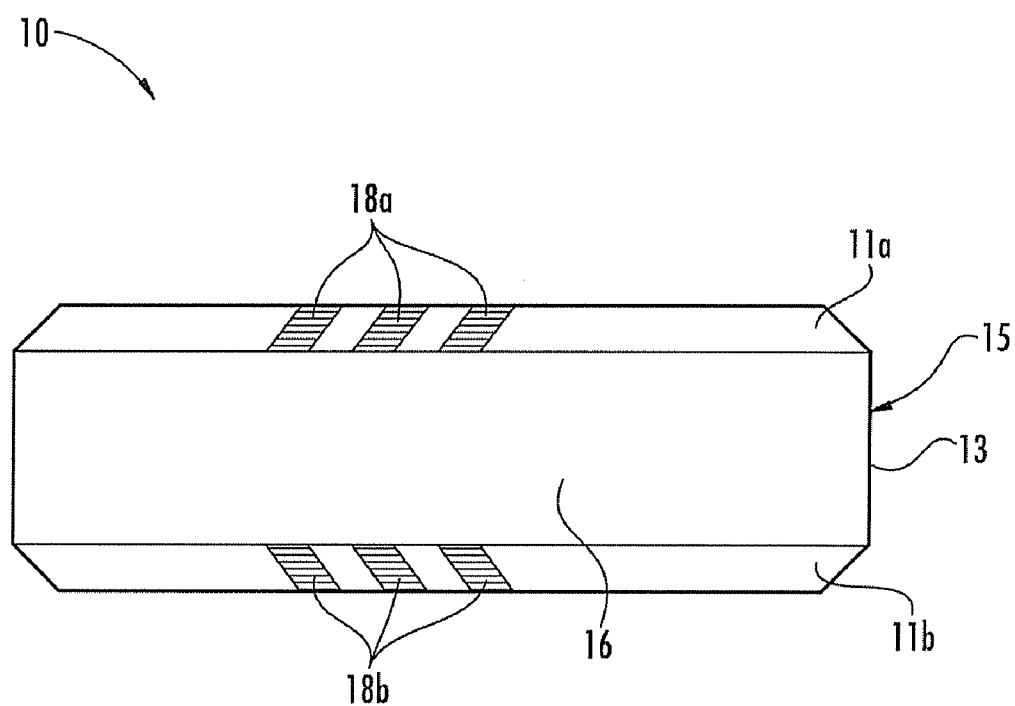
FIG. 2 is a top view of the medical bite block of FIG. 1.

Referring initially to FIGS. 1 and 2, a first embodiment of a medical bite block 10 to be placed intra-orally between a patient's molars, on a side opposite an airway securement such as an ETT, or along side of an LMA which is secured in the midline, is now described. The medical bite block 10 comprises an elongate member 15 having upper and lower longitudinally extending recesses therein 16, 17. Those of skill in the art will appreciate that elongate members of other suitable shapes may be used. The elongate member 15 has a top portion 13 and a bottom portion 14. First and second rounded edges 11a, 11b are illustratively defined in the top portion 13 by the upper recess 16. The first and second rounded edges 11a, lib each have a set of spaced apart transverse notches 18a, 18b respectively defined therein. In other words, the first and second rounded edges 11a, 11b are first and second sidewalls coupled to the elongate member 15, and have first and second sets of transverse notches 18a, 18b defined in an upper surface thereof. The first and second sidewalls 11a, 11b extend above and below the top and bottom of the elongate member 15 and define upper and lower teeth receiving channels. The floors of the upper and lower teeth receiving channels may be flat to limit rotational displacement of the bite block 10 in the patient's mouth if the patient bites down, increasing stability.

The bite block 10 may be of a length and size sufficient to effectively reduce the chance of it being inadvertently lost into the patient's pharynx, thus reducing the risk of airway obstruction by the device. Additionally, the bite block 10 may be of a sufficient length to permit easy grasping for insertion and/or removal by the medical practitioner, even in the event of inadvertent displacement into the patient's pharynx.

As such, the elongate member 15 may have a length of 3" to 6", and a thickness of ½" to 1 ½". The transverse notches 18a, 18b, may be spaced apart by 1/16" to ¼". In addition, the transverse notches 18a, 18b may be 1/16" to ¼" in both length and depth. Of course, those skilled in the art will understand that the elongate member 15 and transverse notches 18a, 18b may have other suitable dimensions.

The notches 18a, 18b receive the canine and/or lateral incisor teeth to positively locate and anchor the bite block 10 in the desired anatomical position in the patient's mouth and to reduce the chance of the bite block sliding out of the patient's mouth. Moreover, the notches 18a, 18b relieve pressure on those canine and lateral incisor teeth when a patient bites down, reducing the possibility of damage to these teeth. This feature will be particularly appreciated by a patient with costly, yet fragile, cosmetic veneers or crowns or by a patient with loose or unstable teeth.

As perhaps best shown in FIG. 2, the notches 18a, 18b are at opposite angles to each other. In other words, the notches 18a are canted at an angle from perpendicular to the elongate member 15, and the notches 18b are canted at an opposite angle thereto. The purpose of the angled notches 18a, 18b is to accommodate the angle that the canine and/or lateral incisor teeth engage the device when placed in the desired and intended anatomical position. This helps to place biting forces on the molars and not the canine and/or lateral incisor teeth, as the molars are more suitable to withstand the biting forces.

The angles may be in a range of 5 to 85 degrees from an axis of the elongate member 15, for example. The notches 18a, 18b each illustratively have a flat bottom and flat sides, although those of skill in the art will understand that the notches may take other shapes.

Although three notches 18a, 18b on each of the first and second rounded edges 11a, 11b are shown, other numbers of notches may be defined in the first and second rounded edges, as will be understood by those of skill in the art. Moreover, the first and second rounded edges 11a, 11b may have the same number of notches 18a, 18b defined therein, or may each have a different number of notches. Furthermore, in some embodiments, either one of or both the first and second rounded edges 11a, 11b may lack notches.

Those of skill in the art will appreciate that the elongate member 15 may be constructed from a compliant material, such as rubber, silicone, plastic, or other suitable materials. A stiff foam or silicone rubber may be an exemplary material from which to construct the elongate member 15 due to its compressibility, which helps to reduce the possibility of dental and oral mucosal irritation, and due to the friction of its surface, which provides adequate traction with teeth to reduce movement when a patient bites down. In some embodiments, the elongate member 15 may be constructed with an embedded crosshatched fiber network to provide enhanced structural support and reduce the possibility of tearing.

Figure 3:
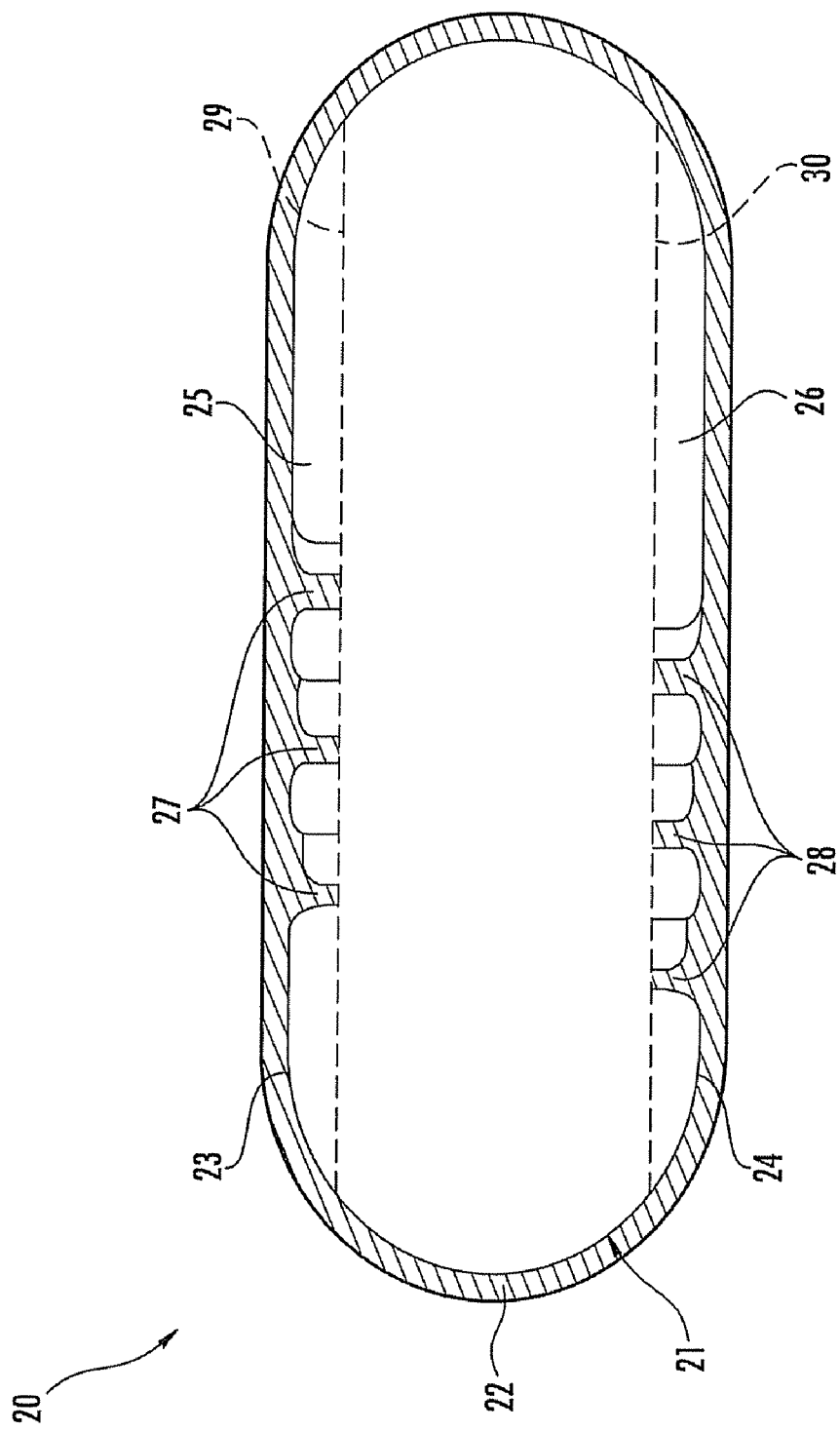
FIG. 3 is a side view of an alternative embodiment of a medical bite block including a surrounding absorptive layer in accordance with the present invention.

With reference to FIG. 3, an alternative embodiment of a medical bite block 20 in accordance with the present invention is now described. The medical bite block 20 comprises an elongate member 21 having upper and lower longitudinally extending recesses therein 29, 30. The elongate member 21 has a top portion 23 and a bottom portion 24. Pairs of top and bottom rounded edges 25, 26 are illustratively defined in the top portion 23 and the bottom portion 24 by the upper and lower recesses 29, 30. The pairs of top and bottom rounded edges 25, 26 each have a set of spaced apart notches 27, 28 respectively defined therein to receive a patient's upper and lower teeth, and to positively locate the medical bite block 20 in the desired anatomical position in the patient's mouth.

In other words, the pairs of top and bottom rounded edges 25, 26 are first and second sidewalls coupled to the elongate member 21, and have first and second sets of transverse notches 27 defined in upper surfaces thereof. The first and second sidewalls 25, 26 extend above and below the top and bottom of the elongate member 21. The first and second sidewalls 25, 26 have third and fourth sets of spaced apart transverse notches 28 defined on lower surfaces thereof.

The notches 27, 28 have curved sides, a rounded top, and a flat bottom to facilitate a secure fit with the patient's teeth and to reduce irritation of the patient's gums. The notches 27 on the top pair of rounded edges 25 are staggered with respect to the notches 28 on the bottom pair of rounded edges 26.

The elongate member 21 is illustratively surrounded by an absorbent layer 22 to absorb oral secretions and to enhance patient comfort and to further facilitate anchoring of the bite block 20 in the intended anatomical position by increasing the friction of the surface, providing added traction with the teeth to reduce movement of the bite block when a patient bites down. The absorbent layer 22 may comprise synthetic gauze. The absorbent layer 22 may also be of cotton or other suitable materials, as will be appreciated by those of skill in the art. In other embodiments, all or part of the absorbent layer 22 may not be present.

Figure 4:
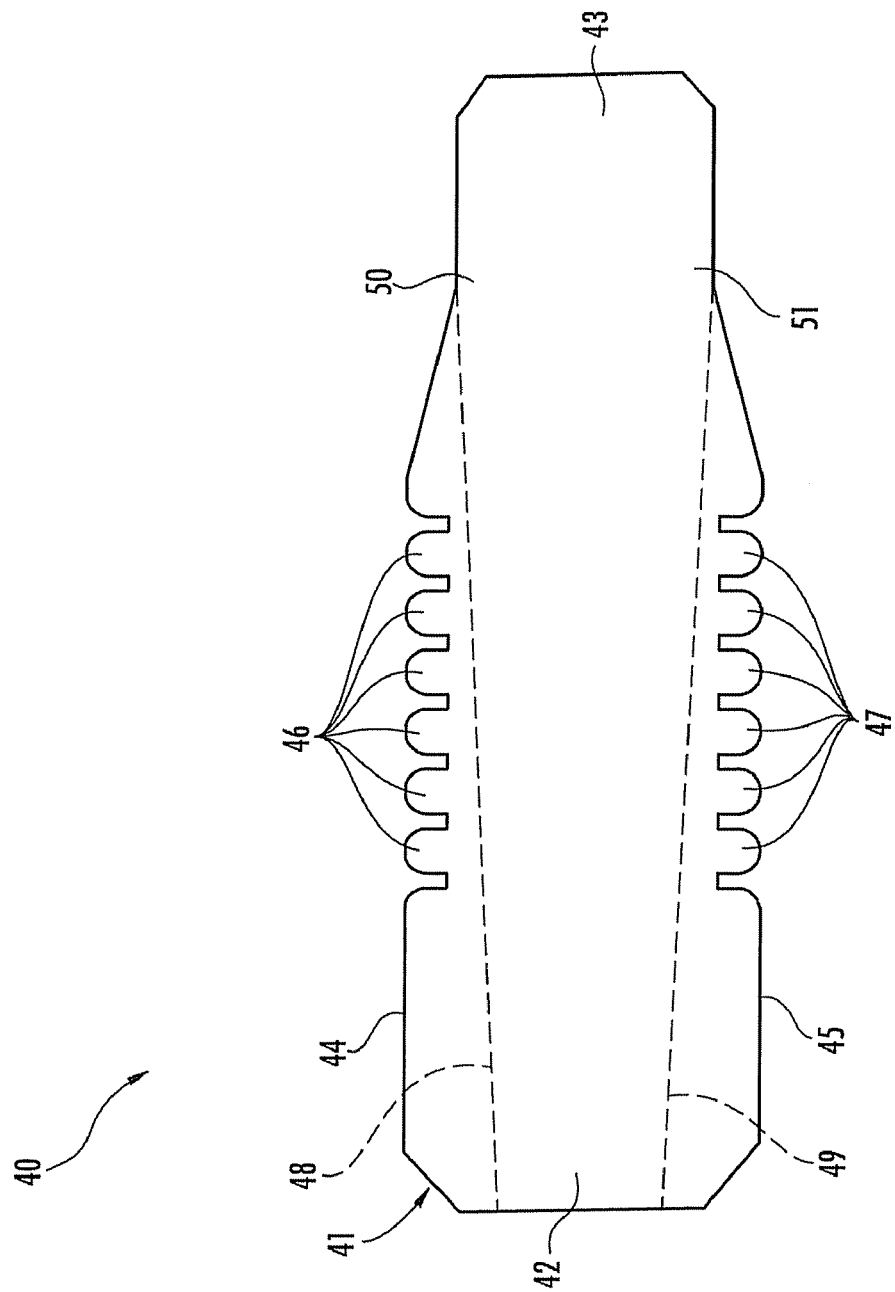
FIG. 4 is a side view of a further embodiment of a medical bite block in accordance with the present invention.
Figure 5A:
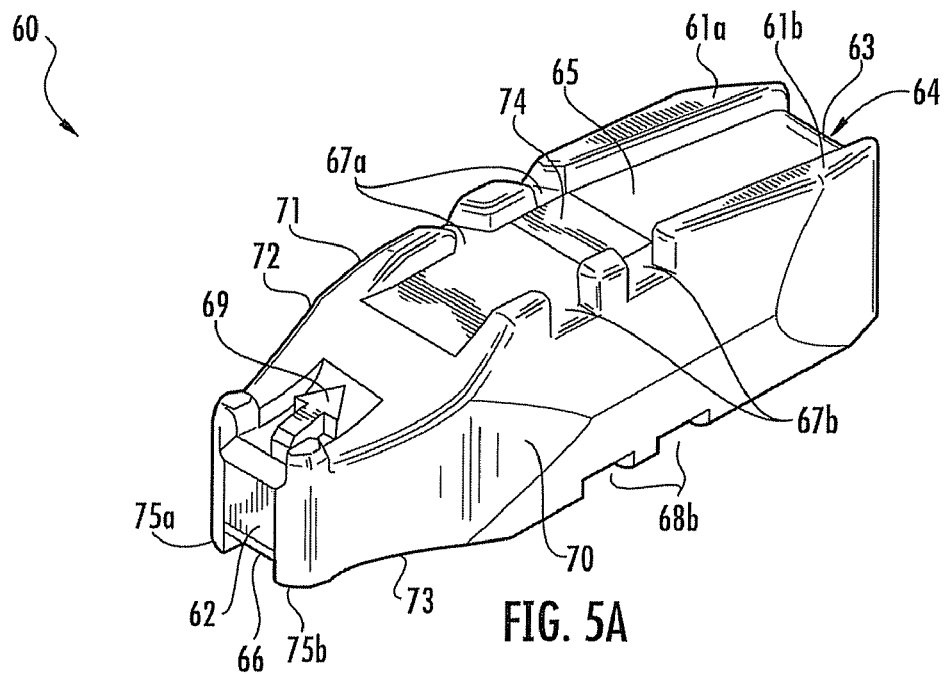
FIG. 5a is a perspective side view of yet another embodiment of a medical bite block in accordance with the present invention.
Figure 5B:
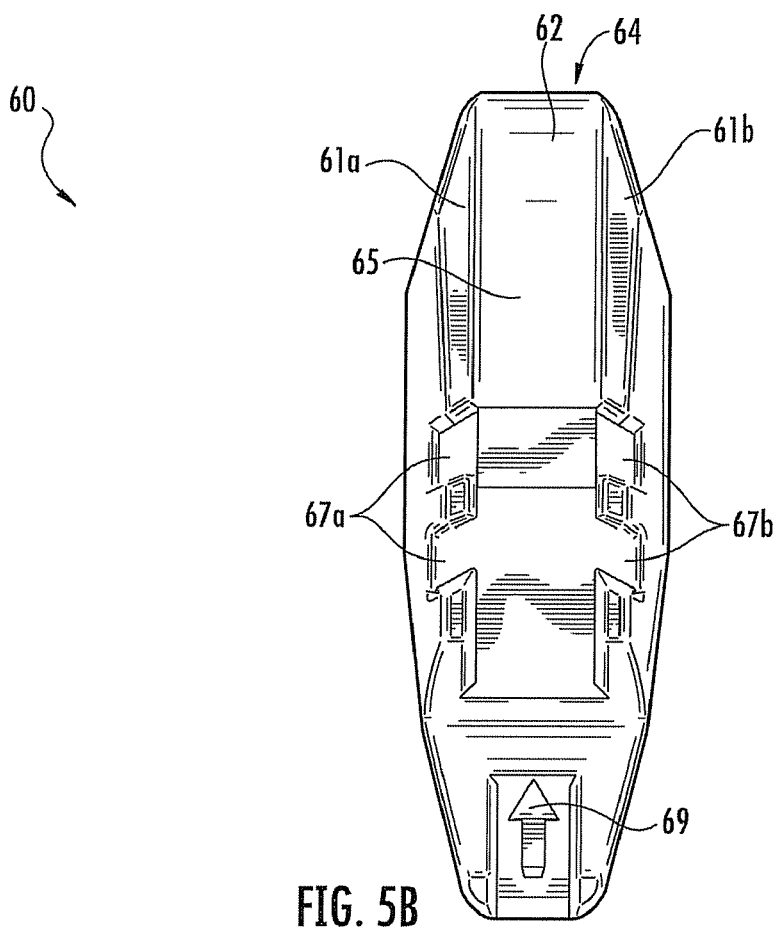
Figure 5C:
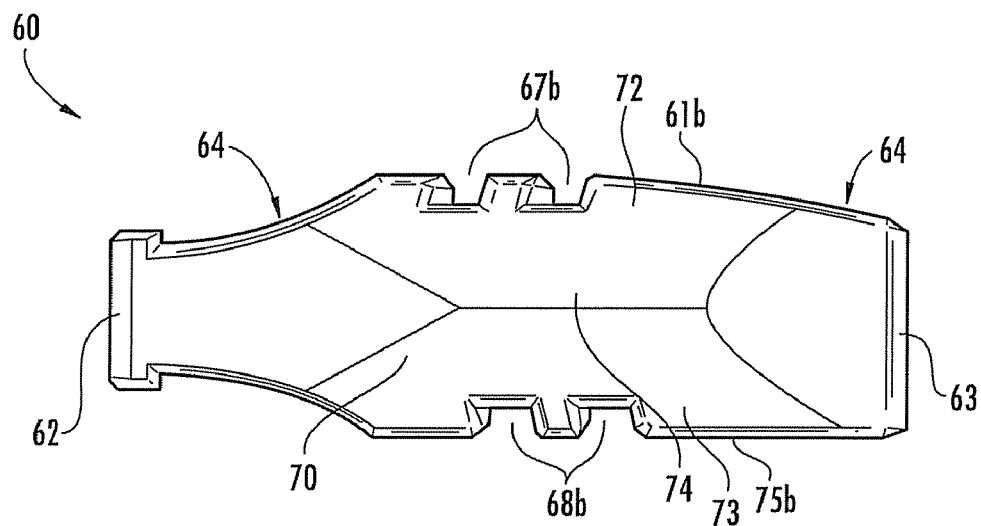
Figure 5D:
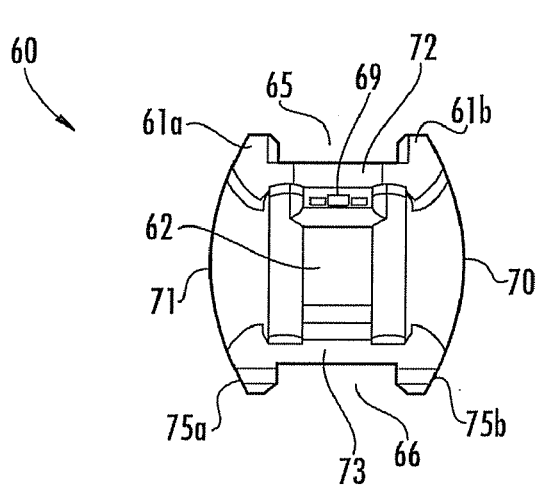
Figure 5E:
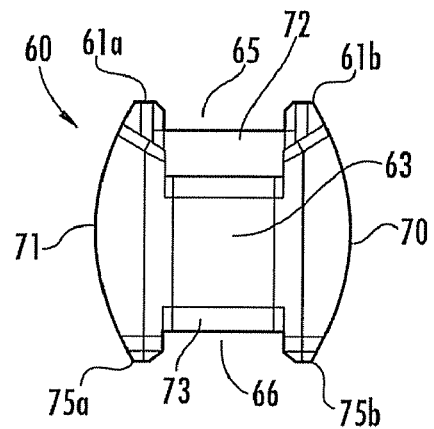

A further embodiment of a medical bite block 40 in accordance with the present invention will now be described with reference to FIG. 4. The medical bite block 40 comprises an elongate member 41 having first and second ends 42, 43, the first end having a thickness less than that of the second end. Moreover, the elongate member 41 has upper and lower longitudinally extending recesses 48, 49 therein. The elongate member 41 has a top portion 50 and a bottom portion 51. Pairs of top and bottom rounded edges 44, 45 are illustratively defined in the top portion 50 and the bottom portion 51 by the upper and lower recesses 48, 49. The pairs of top and bottom rounded edges 44, 45 each have a set of spaced apart notches 46, 47 defined therein to receive a patient's upper and lower canine and/or lateral incisor teeth, and to positively locate and anchor the medical bite block 40 in the desired anatomical position in the patient's mouth. The notches 46, 47 provides an enhanced opportunity for the upper and lower canine and/or lateral incisor teeth to fit therein to help affix the bite block 40 in its intended anatomical position. Those skilled in the art will appreciate that such fixation will help to keep the bite block 40 from slipping out of the mouth of the patient.

In other words, the pairs of top and bottom rounded edges 44, 45 are first and second sidewalls coupled to the elongate member 41, and have first and second sets of transverse notches 46 defined in upper surfaces thereof. The first and second sidewalls 44, 45 also have third and fourth sets of transverse notches 47 defined in lower surfaces thereof. The first and second sidewalls 44, 45 extend above and below the top and bottom of the elongate member 41.

The second end 43 is to protrude beyond the front of a patient's teeth and outside of the mouth when the medical bite block 40 is in place to serve as a handle by which a medical practitioner may securely grasp the medical bite block to remove same from a patient's mouth. The handle formed by the second end 43 may also be used to facilitate insertion of the medical bite block 40 into the patient's mouth and subsequent adjustments to optimize its anatomical position.

Yet another embodiment of a medical bite block 60 is now described with reference to FIGS. 5a-5e. The medical bite block 60 comprises an elongate member 64 having a first end 62, a second end 63, and a medial portion 74 therebetween. The first end 62 has a thickness less than that of the second end 63, and both the first end and the second end taper downward from the medial portion 74. In addition, the elongate member 64 has shaped first and second sides 70, 71 that may facilitate patient comfort, reducing pressure on the patient's lip laterally when in the intended anatomical position. Furthermore, the elongate member 64 has upper and lower longitudinally extending recesses 65, 66 therein. Moreover, the elongate member 64 has a top portion 72 and a bottom portion 73. Pairs of top and bottom shaped edges 61a, 61b and 75a, 75b are illustratively defined in the top portion 72 and bottom portion 73 by the upper and lower recesses 65, 66. In other words, the pairs of top and bottom shaped edges 61a, 61b and 75a, 75b are first and second sidewalls coupled to the elongate member 64 that extend above and below the top and bottom of the elongate member.

The pairs of top and bottom shaped edges 61a, 61b, 75a, 75b each have a set of spaced apart notches 67a, 67b, and 68a, 68b defined therein to receive a patient's upper and lower canine and/or lateral incisor teeth, and to positively locate and anchor the medical bite block 60 in the patient's mouth in the intended anatomical position. The notches 67a, 67b, on the top pair of shaped edges 61a, 61b are staggered and offset with respect to the notches 68a, 68b on the bottom pair of shaped edges 75a, 75b to match the typical arrangement of human teeth, specifically the canines and/or lateral incisors in most cases.

The first end 62 protrudes beyond the front of a patient's mouth when the medical bite block 60 is in place and carries a indicia 69, illustratively a raised arrow, to quickly inform medical practitioners how to orient the medical bite block 60 in a patient's mouth. The indicia 69 is also to intuitively inform the medical practitioner which side is considered the "top" of the bite block 60, although the bite block may be effectively used regardless of orientation. In other words, even if the bite block 60 were placed upside down in the patient's mouth, it would still perform the intended function as a bite block. The first end 62 is to protrude beyond the front of a patient's teeth outside of the mouth when the medical bite block 60 is in place to serve as a handle by which a medical practitioner may securely grasp the medical bite block to remove same from a patient's mouth. The handle formed by the first end 62 may also be used to facilitate insertion of the medical bite block 60 into the patient's mouth and subsequent adjustments to optimize its anatomical position.

Unilateral uses of the bite blocks 10, 20, 40, 60 have been described herein. However, in other embodiments, bilateral uses are envisioned whereby two bite blocks are used and may be joined together by a band of the material of construction for bronchoscopy and endoscopy. This bilateral embodiment may include a gap at an anterior aspect of the connecting band and between the two bite blocks to facilitate the passage of the endoscope or bronchoscope. Method aspects of the invention relate to methods for making the bite blocks 10, 20, 40, and 60 as described herein, as well as to methods of using the bite blocks as will be appreciated by those skilled in the art.

In addition, many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included as readily appreciated by those skilled in the art.

That which is claimed is:

1. A bite block to be positioned between opposing upper and lower teeth in a patient's mouth comprising:
   an elongate member having a top, a bottom, a first end, a second end having a thickness greater than the first end, and a medial portion therebetween, the medial portion having a thickness greater than the second end and the first end, the first end to protrude from the patient's mouth when the bite block is inserted therein; and
   first and second sidewalls coupled to said elongate member on opposite sides thereof, each sidewall extending above and below the top and bottom of said elongate member to define upper and lower teeth receiving channels;
   said first sidewall having a first set of spaced apart transverse notches defined in an upper surface thereof, said second sidewall having a second set of spaced apart transverse notches defined in an upper surface thereof.

2. The bite block of claim 1, wherein said elongate member and said first and second sidewalls comprise a compliant material.

3. The bite block of claim 2, wherein the compliant material comprises foam rubber.

4. The bite block of claim 2, wherein the compliant material comprises silicone.

5. The bite block of claim 1, wherein said first sidewall has a third set of spaced apart transverse notches defined in a lower surface thereof and said second sidewall has a fourth set of spaced apart transverse notches defined in a lower surface thereof.

6. The bite block of claim 1, wherein said first set of spaced apart transverse notches is canted at an angle from perpendicular to said elongate member; and wherein said second set of spaced apart transverse notches are canted at an opposite angle to said first set of transverse notches.

7. The bite block of claim 1, wherein said first and second sidewalls have contoured top and bottom surfaces.

8. The bite block of claim 1, wherein said elongate member and said first and second sidewalls are integrally molded as a monolithic unit.

9. The bite block of claim 1, further comprising an absorbent layer surrounding said elongate member and said first and second sidewalls.

10. The bite block of claim 1, further comprising indicia on said elongate member indicating a desired orientation for the bite block in the patient's mouth.

11. The bite block of claim 1, wherein the first and second sidewalls are of a limited height to minimize contact with the patient's gingiva.

12. A bite block to be positioned between opposing upper and lower teeth in a patient's mouth comprising:
    an elongate member having a top, a bottom, a first end, a second end having a thickness greater than the first end, and a medial portion therebetween, the medial portion having a thickness greater than the second end and the first end, the first end to protrude from the patient's mouth when the bite block is inserted therein; and
    first and second sidewalls coupled to said elongate member on opposite sides thereof, each sidewall extending above and below the top and bottom of said elongate member to define upper and lower teeth receiving channels;
    said elongate member, said first sidewall, and said second sidewall comprising a compliant material;
    said first sidewall having a first set of spaced apart transverse notches defined in an upper surface thereof, and said second sidewall having a second set of spaced apart transverse notches defined in an upper surface thereof;
    said first sidewall having a third set of spaced apart transverse notches defined in a lower surface thereof, and said second sidewall having a fourth set of spaced apart transverse notches defined in a lower surface thereof.

13. The bite block of claim 12, wherein said first set of spaced apart transverse notches is canted at an angle from perpendicular to said elongate member; and wherein said second set of spaced apart transverse notches are canted at an opposite angle to said first set of transverse notches.

14. The bite block of claim 12, wherein said first and second sidewalls have rounded top and bottom surfaces.

15. A method of making a bite block to be positioned between opposing upper and lower teeth in a patient's mouth comprising:
 forming an elongate member having a top, a bottom, a first end, a second end having a thickness greater than the first end, and a medial portion therebetween, the medial portion having a thickness greater than the second end and the first end, the first end to protrude from the patient's mouth when the bite block is inserted therein;
 forming first and second sidewalls coupled to the elongate member on opposite sides thereof, each sidewall extending above and below the top and bottom of the elongate member to define upper and lower teeth receiving channels;
 defining a first set of spaced apart transverse notches in an upper surface of the first sidewall; and
 defining a second set of spaced apart transverse notches in an upper surface of the second sidewall.

16. The method of claim 15, further comprising defining a third set of spaced apart transverse notches in a lower surface of the first sidewall, and defining a fourth set of spaced apart transverse notches in a lower surface of the second sidewall.

17. The method of claim 15, wherein the first set of spaced apart transverse notches is canted at an angle from perpendicular to the elongate member; and wherein the second set of spaced apart transverse notches are canted at an opposite angle to the first set of transverse notches.

18. The method of claim 15, wherein the first and second sidewalls have rounded top and bottom surfaces.

19. The method of claim 15, wherein the elongate member and the first and second sidewalls are formed from a compliant material.

20. The method of claim 15, further comprising surrounding the elongate member and the first and second sidewalls with an absorbent layer.

\* \* \* \* \*